United States Patent [19]

Kastening et al.

[11] 4,151,050
[45] Apr. 24, 1979

[54] PROCESS FOR PRODUCING SULFONES

[75] Inventors: Bertel Kastening; Dierk Knittel, both of Hamburg, Fed. Rep. of Germany

[73] Assignee: Kernforschungsanlage Julich Gesellschaft, Julich, Fed. Rep. of Germany

[21] Appl. No.: 923,328

[22] Filed: Jul. 10, 1978

Related U.S. Application Data

[63] Continuation of Ser. No. 811,678, Jun. 30, 1977, abandoned, which is a continuation-in-part of Ser. No. 647,812, Jan. 9, 1976, Pat. No. 4,053,402, which is a continuation-in-part of Ser. No. 474,167, May 29, 1974, Pat. No. 3,980,535.

[30] Foreign Application Priority Data

| Jun. 2, 1973 [DE] | Fed. Rep. of Germany | 2328196 |
| Jan. 10, 1975 [DE] | Fed. Rep. of Germany | 2500727 |
| Jun. 20, 1976 [DE] | Fed. Rep. of Germany | 2629320 |

[51] Int. Cl.² ............................................. C25B 3/04
[52] U.S. Cl. .................................. 204/59 R; 204/72; 260/607 AL
[58] Field of Search ........................... 204/59 R, 72; 260/607 AL

[56] References Cited

U.S. PATENT DOCUMENTS

| 3,344,047 | 9/1967 | Neikam | 204/59 R |
| 3,764,492 | 10/1973 | Baizer et al. | 204/59 R |

OTHER PUBLICATIONS

Knittel et al., J. Applied Electrochemistry, vol. 3, pp. 291–296 (1973).
Knittel et al., Berichte Bunsen-Geselschaft fur Physikalische Chemie, vol. 77, pp. 833–836 11/73.

*Primary Examiner*—F. C. Edmundson
*Attorney, Agent, or Firm*—Karl F. Ross

[57] ABSTRACT

A process for producing sulfones in which sulfur dioxide is electrolytically transformed into $SO_2^-$ ions and caused to react with organic compounds having functional groups replaceable by $SO_2^-$, in an aprotic organic solvent, to produce the corresponding organosulfone. According to the present improvement a phosphoric acid triester such as phosphoric acid tribenzyl ester, is added to the solvent as an organic compound capable of reacting with halogen ions of a salt, such as tetraalkylammoniumhalogenide or tetraalkylphosphoniumhalogenide, introduced into the solvent as a conductivity-promoting agent.

8 Claims, 1 Drawing Figure

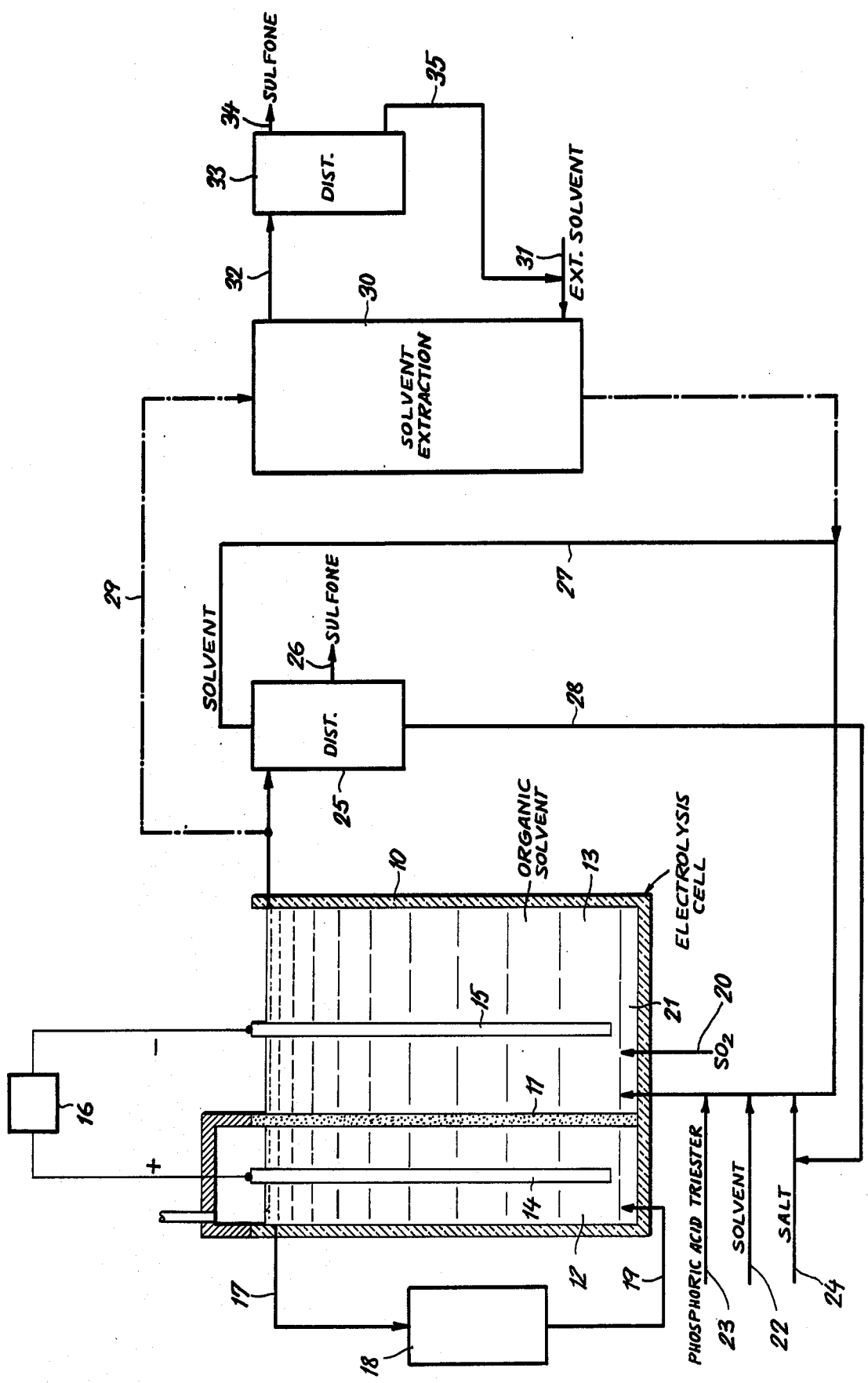

PROCESS FOR PRODUCING SULFONES

CROSS REFERENCE TO RELATED APPLICATIONS

This is a continuation of application Ser. No. 811,678, filed 30 June 1977, now abandoned; which was a continuation-in-part of our application Ser. No. 647,812 filed Jan. 9, 1976 (U.S. Pat. No. 4,053,402) and, in turn, a continuation-in-part of Ser. No. 474,167 filed 29 May 1974 and entitled PROCESS FOR PRODUCING SULFONES, now U.S. Pat. No. 3,980,535.

FIELD OF THE INVENTION

The present invention relates to a process for the production of organosulfones or mixtures of sulfones and, more particularly, to improvements in the process described in our earlier application and Letters Patent identified above.

BACKGROUND OF THE INVENTION

Organosulfones are useful in a number of fields, e.g. the manufacture of plastics (synthetic resins) and fabric finishing, as additives to textile fibers, as dyestuffs or dyeing aids, and as therapeutic compounds in a variety of processes and treatments. Sulfones are particularly convenient surface-active agents in the chemical process arts.

Prior to the system described in the abovementioned copending application, sulfones were made principally be several different techniques whereby an organic compound R—X was reacted with sodium sulfide (Na$_2$S) to yield the organic sulfide R—S—R in accordance with the formula:

$$2R-X + Na_2S \rightarrow R-S-R + 2NaX$$

In this relationship, X is generally a halogen atom, S is sulfur and R is the organic radical.

The organosulfide R—S—R is oxidized in a second stage to the sulfone with an oxidizing medium or by catalytic oxidization in a reaction which can be represented by the formula:

$$R-S-R + O_2 \rightarrow R-SO_2-R$$

where the reaction product is the sulfone.

These processes and others known in the art not only required a plurality of steps, but frequently isolation of intermediates, such as the organosulfide before subsequent steps were undertaken. Such processes are neither economical nor convenient and were time consuming and frequently had poor yields.

These disadvantages were overcome in the system described in the aforementioned Letters Patent which, in turn, is developed further in our publication Elektrosynthese Symmetrischer Und Unsymmetrischer Sulfone, *Berichte der Bunsen-Gesellschaft fur Physikalische Chemie* (earlier *Zeitschrift fur Elektrochemie*), Volume 3, 30 Nov. 1973, and our publication entitled Electrosynthesis of Sulfones, *Journal of Applied Electrochemistry*, Volume 3 (1973), pages 291 to 295.

In our system as described in U.S. Pat. No. 3,980,555 sulfones are produced in a single-stage reaction by electrolyzing sulfur dioxide in an aprotic organic solvent in which the organic compound R—X is soluble and which is provided with a salt for promoting conductivity of the solvent. The electrolysis produces SO$_2^-$ ions which can replace the X groups of the organic compound.

As described in U.S. Pat. No. 3,980,535, the process for the production of sulfones utilizes the fact that the SO$_2^-$ ion can replace certain functional groups of an organic compound in an organic medium (nonaqueous solvent) in which the SO$_2^-$ ion is produced by electrolysis. While the atoms or groups of a number of organic compounds have been found to be replaceable by SO$_2^-$ ions formed by electrolysis of SO$_2$ in the organic medium, the compounds which are found to be most reactive for this purpose are the organic halogen compounds (i.e. compounds of the formula R—X in which X is chlorine, bromine or iodine), the sulfuric acid esters and the sulfonic acid esters. Thus X may also represent sulfuric acid ester group or the sulfonic acid ester group.

The overall reaction, therefore, can be represented by the formula:

$$2e^- + 2R-X + SO_2 \rightarrow R-SO_2-R + 2X^-$$

where the electrolysis reaction is represented by the addition of electrons to the reaction system, ultimately resulting in the formation of ions of the replaced functional groups. The product is, of course, the organosulfone R—SO$_2$—R.

As noted, the reaction is carried out in an aprotic organic solvent (nonaqueous medium) containing a salt, preferably a quaternary ammonium salt, designed to provide the necessary conductivity for the electrolysis current which transforms the SO$_2$ into SO$_2^-$. Preferably the salt is a tetraalkylammonium salt such as tetramethyl or tetraethylammoniumchloride or bromide.

The organic compound is introduced into the medium or constitutes the reaction vehicle in which the sulfur dioxide is dissolved and the system is then subjected to electrolysis. Of course, a system in which the organic compound is in liquid form and can constitute the reaction medium or vehicle as well as one of the reactants, has the advantage that recovery of the sulfone is simplified. Organic compounds which can operate in this manner are dimethylsulfate, chloroacetonitrile and chloroacetone. The latter compounds require no separate solvent.

It has been found to be advantageous to prevent the electrolysis current from exceeding the maximum usable current density that produces only the SO$_2^-$ ions. This can be accomplished by providing in the electrolysis cell a reference electrode which is not traversed by the electrolysis current and controlling the voltage between the reference electrode and the cathode so that with respect to the standard potential of the sulfur dioxide/sulfur anion REDOX couple (SO$_2$/SO$_2^-$), the potential does not exceed 0.1 volt. It has been found that best results are obtained when the sulfur dioxide concentration in the solution during electrolysis is at least 0.1 mole/liter The process also has the significant advantage that it is possible to produce polymeric sulfones readily. It is only necessary, to this end, to use an organic compound of the type X—R—X where R is a difunctional organic radical and X is an atom or group replaceable by SO$_2^-$. The reaction follows the overall formula:

$$2n(X-R-X) + 2n(SO_2) + 4ne^- \rightarrow +R-SO_2-R-SO_2+_n + 4nX^-$$

where n is an integer, e$^-$ is the electronic charge, R and X have their earlier-stated meanings, and $-\!(\!R\!-\!SO_2\!-\!R\!-\!SO_2\!)\!-$ is the repeating group of the polymer.

Of course cyclic sulfones can also be produced from organic compounds having terminal X groups, the C atoms to which they are attached being bridged by the $-SO_2-$ group.

It has been found to be most advantageous to carry out the reaction in an electrolysis cell subdivided by a diaphragm or ion-exchange membrane into a cathode compartment and an anode compartment. When an anion ion-exchange membrane is used, the current through the cell is brought about solely by migration of the anions $X^-$ liberated by the cathodic process. The anions traverse the membrane and are oxidized by the anode. When X is a halogen atom, preferably chlorine or bromine, the halogen $X_2$ is liberated at the anode as the free halogen. The sulfone is formed in the cathode compartment. The system has been found to reduce side reactions which might tend to form impurities. A cell of the character described has been found to have an especially high yield of sulfones.

In the process of the present invention, the sulfones or sulfone mixtures can be separated from the solvent by the distillation or by extraction with the extraction effluent then being distilled. For the extraction solvent, it is preferred to use a compound in which the salts (provided for conductivity) are insoluble. Such a solvent may be chloroform or petrolether. The salt recovered in this manner may be recycled to the cell and even the free halogen may be used in ancillary chemical reactions.

OBJECT OF THE INVENTION

It is the object of this invention to improve upon the process described in the aforementioned copending application and the earlier Letters Patent.

SUMMARY OF THE INVENTION

We have now found that it is possible to improve the efficacy and economy of the process described in the aforementioned application by providing, in the aprotic solvent, a phosphoric acid triester, capable of reacting with the halogen ion of the conductivity-promoting salt resulting, by substitution of the acid group of the ester by halogen (chloride, bromine, iodine) atom, in an organic halogen compound which participates in the sulfone-forming reaction.

Thus the essential feature of the present improvement is the provision of an organic compound (namely a phosphoric acid triester) in the aprotic organic solvent which is capable of forming an organic halogen compound with the halogen ion of the conductivity-promoting salt in place of or in addition to the sulfonic acid esters or esters of organic oxygen-containing acids of the aforementioned copending application.

According to the invention, polymeric sulfones may be produced in accordance with the relationship:

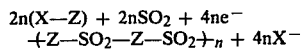

where Z is a difunctional organic radical, X is a halogen (e.g. chlorine, bromine or iodine), $e^-$ is the electronic charge, $X^-$ is the halogen ion and n is an integer representing the number of repeating units in the polymer.

The process is carried out in an electrolysis cell which is subdivided by a diaphragm or an anion-exchange membrane into a cathode compartment and an anode compartment. The current flow is primarily by migration of the anion $X'$ set free by the cathodic process and transported to the anode compartment. The anions are oxidized at the anode. The sulfone is recovered from the cathode compartment. The use of such an electrolysis cell has been found to give an especially high yield of sulfones and the $SO_2^-$ ions are found to react with the organic compound directly and practically simultaneously with their formation upon electrolysis. The sulfones are separated from their solution in the solvent by distillation or extraction. Preferably the extraction is carried out with a solvent in which the conductivity-promoting salt is insoluble, such as chloroform or petrolether.

BRIEF DESCRIPTION OF THE DRAWING

The above and other objects, features and advantages of the present invention will become more readily apparent from the following description, reference being made to the accompanying drawing in which the sole FIGURE is a flow diagram illustrating the invention.

SPECIFIC DESCRIPTION

In the drawing, there is shown an electrolysis cell 10 which is subdivided by an anion exchange membrane 11 into an anode compartment 12 and a cathode compartment 13 respectively containing the anode 14 and the cathode 15. A source of constant direct current 16 is connected across the electrodes 14, 15. The electrolyte contained in the anode compartment 12 is led at 17 to a halogen remover 18 where the halogen generated at the anode 14 is removed by extraction or distillation from the electrolyte, the latter being recycled at 19 to the anode compartment 12. Sulfur dioxide gas is introduced at 20 into the organic medium 21 within the cell, the medium consisting of a solvent introduced at 22; the organic compound is introduced at 23 and the conductivity-promoting salt is introduced at 24.

The reaction products are led into a distilling column 25 from which the sulfone is recovered (i.e. obtained or withdrawn) at 26, solvent is recovered at 27 and recycled to the cell, and the salt is recovered at 28 and likewise recycled.

Alternatively, the reaction products may be led at 29 to a solvent-extraction column 30 into which the extraction solvent is introduced at 31. The extract is withdrawn at 32 and subjected to distillation at a column 33 to recover (i.e. obtain or withdraw) the sulfone at 34 and solvent at 35, the latter being recycled to the extraction stage.

More particularly, it is an object of the present invention to improve the economy of the process for producing sulfones described in the aforementioned copending application and the earlier Letters Patent by increasing the range of starting materials which can be used.

This is achieved in accordance with the present invention by providing, as additives to the process of the aforementioned patent, both a salt capable of forming halogen ions and a phosphoric acid triester. Both are soluble in the solvent in the compartment in which the sulfone is formed.

The sulfone formation results from a reaction between $SO_2^-$ (formed in the electrolyte by cathodic reduction of sulfur dioxide to the sulfur dioxide anion) and the molecules of the organic compound RX resulting in the solution from the reaction of the phosphoric acid triester (dealkylation) with the halogen ions in accordance with the relationship:

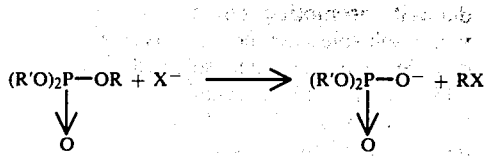

As has been pointed out in "*Methoden der organischen Chemia/Houben-Weyl*", E. Muller, Stuttgart, 1964, volume XII/2 Part 2, Pages 256 through 258, the reactivity of the reactants is strongly influenced by the nature of the nonparticipating "alcohol" radicals (R'O—). Thus it is an important advantage of the process of the present invention that the sulfones (R—SO$_2$—R) with alkyl moieties (R—) can be made from a wide range of additional starting materials not hitherto contemplated, namely, phosphoric acid triesters, with greater selectivity and increased reactivity. It is of particular advantage that it allows halogen compounds RX to be made in situ which could not be readily made heretofore.

The process of the present invention is, as already noted, also suitable for the production of polymeric sulfones in accordance with the relationship:

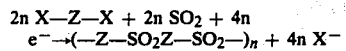

In this formula Z is a divalent organic moiety and X is the halogen as described. To form the reactive molecule X—Z—X, phosphoric acid can be esterified with a difunctional alcohol in accordance with the relationship:

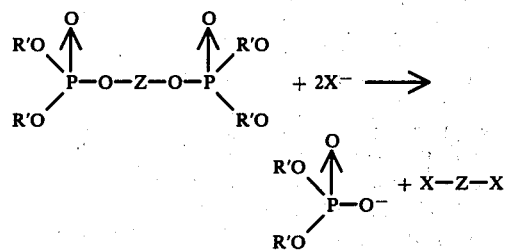

A further advantage of the process of the present invention resides in that cyclic sulfones can be produced. This can be achieved simply be using an ester having such a divalent moiety (previously identified as Z), such that between the two bonding locations there is provided an alkyl chain of such length that the cyclic sulfone

can be formed without internal stress. The chain between bonding locations will customarily be between 4 and 6 members, e.g. carbon atoms, oxygen atoms and/or nitrogen atoms.

The process according to the present invention gives a high yield as well as a relatively high current efficiency and selectivity.

SPECIFIC EXAMPLE

For the production of dibenzylsulfone, we make use of an electrolysis cell as described and subdivided by an anion ion-exchange membrane into a cathode compartment and an anode compartment. The anode is glassy carbon electrode and the cathode is platinum with an effective surface area of 9 cm$^2$. The solvent is acetylnitrile and the conductivity-increasing and halogen-ion forming salt is tetraethylammonium iodide which is introduced with a concentration of 0.2 moles per liter.

Similar tests were carried out with tetraalkylphosphoniumhalogenide, tetraarylammoniumhalogenide and tetraarylphosphoniumhalogenide the halogens being chlorine, bromine and iodine, the alkyl groups being C$_1$–C$_6$ straight and branched chain radicals and the aryl groups being phenol and alkyl substituted phenol with the alkyl group being straight or branch chain with 1 to 6 carbon atoms.

The solvent was contained in the cathode compartment as well as in the anode compartment.

Sulfur dioxide was dissolved in the solvent in the cathode compartment to a concentration of about 0.5 moles per liter, corresponding to the saturation at a working temperature of 70° C.

The phosphoric acid triester, which reacted with the iodide ion in solution to form the organic halogen compound for sulfonation, was phosphoric acid tribenzylester and was introduced in a concentration of 0.1 mole per liter.

Electrolysis was carried out with a current density of 40 mA/cm$^2$ at a temperature of 70° C. After the passage of 1500 coulombs, the electrolysis was terminated.

The solution in the cathode chamber was distilled to eliminate the solvent and the residue was dissolved in water and chloroform. Distillation of the chloroform from the fractionally separated chloroform phase produced crystalline dibenzylsulfone. The chemical yield of the dibenzylsulfone, with respect to the starting quantity of phosphoric acid triester, amounted to 61% of theoretical and the yield (current efficiency) was about 42% of theoretical value.

The wide range of additional phosphoric acid triaryl and trialkyl esters were tested similarly and all were found to react effectively. Including among them was phosphoric acid tributyl ester, phosphoric acid tritolyl ester and phosphoric acid triethyl ester.

The critical parameters of the present process in terms of current density and cell voltage are determined by providing in the electrolysis cell a reference electrode which is not traversed by the electrolysis current and controlling the voltage between the reference electrode and the cathode so that, with respect to the standard potential of the SO$_2$/SO$_2^-$ Redox couple, the potential does not exceed 0.1 volt. As in the system of the prior application, best results are obtained when the sulfur dioxide concentration in solution is at least 0.2 mole/liter. The maximum effective sulfur dioxide concentration is the solubiity limit of SO$_2$ in the solution.

The temperature at which the reaction is carried out can be between the freezing point and boiling point of the solution although best results are obtained between room temperature (about 20° C.) and the boiling point of the solution. Elevated temperatures i.e. temperatures above room temperature, improve the results over lower temperatures although there is no specific range which can be defined as giving optimum results. For example, excellent results are obtained between 30° C. and the boiling point of the solution.

In general a temperature of about 60 to 90° C., preferably about 80° C. has proved to be the best mode.

The solvent can be any aprotic organic solvent in which the salt, the organic ester and the sulfur dioxide are soluble and which will not engage in electrolytic actions adverse to the desired reaction. Best results are obtained with acetonitrile, dimethylformamide and dimethyl sulfoxide.

As far as the concentration of the salt and other reactants are concerned, it should be noted that the preferred concentration of the ester is at least 0.1 molar up to the saturation limit of this compound in the solvent. The salt should be present in at least equimolar concentration with the ester and thus should also be present in a minimum concentration of 0.1 normality up to a normality or molarity corresponding to the saturation limit of the ester.

We claim:

1. In a process for producing a sulfone in which sulfur dioxide solubilized in an aprotic solvent is electrolyzed with substantially the maximum current density that produces only $SO_2^-$ ions and with a voltage that does not exceed substantially 0.1 volt with reference to the standard potential of the $SO_2/SO_2^-$ redox couple, the resulting sulfur dioxide anion being reacted at a temperature between the freezing and boiling points of the solution with an organohalogen compound, the improvement wherein said organohalogen compound is formed in situ in said electrolyte by the reaction of a halogen-ion-forming salt and a phosphoric acid triester where the halogen is selected from the group which consists of chlorine, bromine and iodine, said halogen-ion-forming salt being selected from the group which consists of tetraalkylammoniumhalogenide, tetraalkylphosphoniumhalogenide, tetraarylammoniumhalogenide and tetraarylphosphoniumhalogenide.

2. The improvement defined in claim 1 wherein said salt is selected from the group which consists of tetraethylammoniumiodide, tetraethylammoniumbromide and tetrabutylphosphoniumchloride.

3. The improvement defined in claim 1 wherein said phosphoric acid triester is phosphoric acid tribezyl ester.

4. A process for producing a sulfone which comprises the steps of:

(a) introducing into the cathode compartment of an electrolysis cell subdivided into an anode compartment and a cathode compartment, a reaction system comprising an aprotic organic solvent, a conductivity-promoting salt soluble in said solvent which salt releases halogen ions therein, and sulfur dioxide, said salt being selected from the group which consists of tetraalkylammoniumhalogenide, tetraalkylphosphoniumhalogenide, tetraarylammoniumhalogenide, and tetraarylphosphoniumhalogenide;

(b) electrolyzing said reaction system at a current density, temperature and voltage sufficient to transform said sulfur dioxide into $SO_2^-$ ions with substantially the maximum current density that produces only $SO_2^-$ ions and with a voltage that does not exceed substantially 0.1 volt with reference to the standard potential of the $SO_2/SO_2^-$ redox couple;

(c) reacting at a temperature between the freezing and boiling points of the solution the $SO_2^-$ ions formed in step (b) with an organic halogen compound formed in situ in said reaction system by the reaction of halogen ions of said salt with a phosphoric acid triester where the halogen is selected from the group which consists of chlorine, bromine and iodine, thereby producing the corresponding organosulfone in said cathode compartment; and (d) separating said organosulfone from said solvent.

5. The process defined in claim 4 wherein said salt is selected from the group which consists of tetraethylammoniumiodide, tetraethylammoniumbromide and tetrabutylphosphoniumchloride.

6. The process defined in claim 5 wherein said phosphoric acid triester is phosphoric acid tribenzyl ester.

7. The process defined in claim 4 wherein the organosulfone is recovered from the solvent by evaporating the solvent from the reaction system of said cathode compartment, treating the evaporation residue with water and chloroform, separating the chloroform phase from the water phase, and driving chloroform out of said chloroform phase recover the organic sulfone.

8. The process defined in claim 4, wherein the organosulfone is recovered from the solvent by extracting the reaction system of said cathode compartment with a liquid and subjecting the extraction liquid to distillation.

* * * * *